United States Patent [19]

Fourman

[11] Patent Number: 4,559,225

[45] Date of Patent: Dec. 17, 1985

[54] SUNSCREEN COMPOSITION

[76] Inventor: Robert G. Fourman, P.O. Box 274, Plainsboro, N.J. 08536

[21] Appl. No.: 580,748

[22] Filed: Feb. 16, 1984

[51] Int. Cl.[4] ............................ A61K 7/42; A61K 7/44
[52] U.S. Cl. ........................................... 424/59; 424/60
[58] Field of Search ..................................... 424/59, 60

[56] References Cited

FOREIGN PATENT DOCUMENTS 0055857 7/1982 European Pat. Off. ............... 424/60
2109703 9/1981 Fed. Rep. of Germany ........ 424/59

OTHER PUBLICATIONS

Kass, Cosmetics & Toiletries, 3/1976, vol. 91.
Wetterhahn, Cosmetics & Toiletries, 3/1980, vol. 95, pp. 31 to 33.

Primary Examiner—Dale R. Ore
Attorney, Agent, or Firm—Kevin B. Clarke

[57] ABSTRACT

Water-proof sunscreen compositions, including a cellulosic polymer, a solvent, an ultra-violet sunscreening agent and an emollient are disclosed. The compositions when spread on the skin leave an elegant non-greasy, non-tacky film with a superior resistance to removal by water and which provide prolonged high level protection for human skin to ultraviolet radiation.

5 Claims, No Drawings

SUNSCREEN COMPOSITION

This invention relates to sunscreen compositions which when applied to human skin provide protection against erythema caused by ultraviolet radiation from sunlight. More particularly, this invention relates to sunscreen compositions capable of protecting the skin against erythema over prolonged periods of time.

Excessive exposure of human skin to either the rays of the sun or to sun lamps which emit ultraviolet radiation, similar to natural sunlight can result in sunburn or erythema solare as the condition is medically defined.

In order to substantially reduce or entirely prevent sunburn, various compositions have been proposed which contain components which scatter the sunlight effectively or which absorb the erythemal part of the suns radiant energy i.e. ultraviolet energy radiations equivalent to about 2800 to about 4000 angstrom units.

The conventional light scattering materials which are incorporated into suntan preparations in either dry form or with suitable vehicles are talc, zinc oxide, kaolin, calcium carbonate, magnesium oxide and titanium dioxide.

Sunscreen compositions now generally available are formulated in the form of creams, lotions and oils containing as the active agents ultraviolet light absorbing chemical compounds. The active chemical compounds act to block the passage of erythematogenic radiation, by absorption, thereby preventing its penetration into the skin.

For topical application, sunscreen compositions must be non-toxic and non-irritating to the skin tissue and capable of application to the skin as a uniform continuous film. In addition, the active sunscreening agents must be chemically stable and in particular must be resistant to chemical and photodegradation when on the skin as well as resistant to absorption through the skin. Among the widely used ultraviolet absorbing sunscreening agents meeting the aforesaid conditions are: oxybenzone (2-hydroxy-4-methoxy benzophenone); dioxybenzone (2,2'-dihydroxy-4-methoxy benzophenone); octyldimethyl PABA (octyl-dimethyl-para amino benzoate); amino benzoic acid; cinoxate (2-ethoxyethyl-p-methoxycinnamate); diethanolamine-p-methoxycinnamate; digalloyl trioleate ethyl 4- bis (hydroxypropyl) aminobenzoate; 2-ethylhexyl- 2-cyano-3,3-diphenylacrylate; ethylhexyl-p-methoxycinnamate; 2-ethylhexyl salicylate; glyceryl aminobenzoate; homosalate (3,3,5-trimethylcyclohexyl salicylate); triethanolamine salicylate; 2-phenylbenzimidazole-5-sulfonic acid; sulisobenzone (5-benzoyl-4-hydroxy-2-methoxy-benzenesulfonic acid); padamate A (pentylester of 4-(dimethylamino) benzoic acid); padamate 0 (2-3thylhexylester of 4 - (dimethylamino) benzoic acid); and the combination of 2-hydroxy-1, 4-naphthalenedione with dihydroxyacetone.

Each of the foregoing compounds have been used alone or in combination in various sunscreen compositions and been found to provide varying sun protection factors (SPF) when evaluated in human subject utilizing standard solar simulator tests.

In addition to being chemically stable, in order to maintain their effectiveness, sunscreen compositions must also be resistant to removal from the skin by perspiration, skin oil or water.

Various U.S. Pat. Nos. such as 4,264,581; 4,193,989; 3,864,473; 3,529,055 and 3,506,758 address the problems encountered in preparing water resistant sunscreen compositions.

It is an object of the present invention to provide sunscreen compositions which have high protection factors (SPF), are highly resistant to removal by water and which when applied to the skin leave an elegant, non-tacky, non-sticky film.

In accordance with the present invention there are provided novel stable sunscreen compositions which resist removal by water, as determined by standard wash-off tests. Such sunscreen compositions provide prolonged (SPF from 2 to about 20) protection for very fair, sun-sensitive skin that normally burns easily.

The compositions of the present invention comprise a filmforming cellulosic polymer; a solvent; an ultraviolet sunscreening agent; an emollient and optionally, a plasticizing agent. In addition, the compositions may include small but effective amounts of opacifiers, surfactants, fragrances and other compatible agents to obtain desired cosmetic aesthetics.

The film-forming cellulosic polymer is desirably a cellulose ether which is present in the sunscreen compositions of the present invention in amounts ranging from 0.1% to 10.0%, preferably 0.5% to 4.0% by weight of the total composition. The preferred cellulose ether is a cellulose ethyl ether having an ethoxy content about 43%.

The solvent is a solvent for the cellulosic polymer and is preferably an aliphatic alcohol such as ethanol propanol or isopropanol which is present in amounts ranging from 10.% to 90.0%, preferably 30.0% to 75.0% by weight of the total composition.

The emollient materials are selected from among the hydrocarbon oils and waxes, as well as fatty acid esters of low molecular weight alchohols such as butyl stearate, isopropyl stearate, isopropyl palmitate, isopropyl myristate and volatile silicone fluids composed of low molecular weight dimethyl siloxanes that have been assigned CTFA name cyclomethicone and are exemplified by Volatile Silicone 7207, a trademarked product of Union Carbide Corporation and the following trademarked products of Dow Corning Corporation: Dow Corning 244 Fluid and Dow Corning 245 Fluid. The emollient material is present in amounts ranging from 5.0% to 60.0%, preferably 20.0% to 45.0% by weight of the total composition.

The ultraviolet absorbing sunscreen is compatible with the emollients and desirably dissolved therein whereby clear, preferably water-white, compositions are obtained. The sunscreen material is selected from the group comprising the pentyl and 2-ethylhexylesters of 4-(dimethylamino) benzoic acid; dioxybenzone; ethylhexyl-p-methoxy-cinnamate; ethyl 4- bis (hydroxypropyl) aminobenzoate; 3,3,5-trimethylcyclohexyl salicylate; 2-ethylhexyl-2-cyano-3,3-diphenylacrylate; 2-ethylhexyl-2-cyano-3,3-diphenylacrylate; 2-ethylhexyl salicylate and mixtures thereof. The sunscreen material is present in amounts ranging from 1.0% to 20.0%, preferably 4.0% to 11.0% by weight of the total composition.

In the event a volatile silicone fluid is employed as the aforesaid emollient, a further desirable component in the sunscreen compositions of the present invention is a plasticizer for the cellulose film. The plasticizer is preferably selected from among the silicone resins listed under the CTFA name Dimethicones. The plasticizers are to be distinguished from the previously disclosed cyclomethicone volatile fluids in that the latter are low molecular weight, volatile dimethyl siloxanes whereas the former are higher organic content polymethyl siloxanes, polyphenylsiloxanes and combinations of polymethylsiloxanes with trimethyl siloxysilicate exemplary materials are available from The General Electric Company under the Trademark GE Silicone 4267 and Dow Corning Company under the trademarks Dow Corning 225 Fluid; Dow Corning 556 Fluid and Dow Corning 1107 Fluid and Union Carbide under the trademark Union Carbide Silicone L-45.

If present in the composition the plasticizer may be included in amounts ranging from about 1.0% to 10.0%, preferably from about 4.0% to 8.0% by weight of the total composition.

In addition the compositions of this invention may include small but effective amounts of opacifiers, fragrances, surfactants, preservatives and other desirable and compatible agents to obtain desired cosmetic aesthetics.

The water-proof sunscreen compositions of the present invention may be formulated by simply admixing all of the components. However, it is preferred to first dissolve the cellulosic material in the solvent prior to admixing with the remaining components.

The example which follows sets forth the preferred embodiment of the present invention:

EXAMPLE

| Ingredient | % w/w |
|---|---|
| Ethanol (anhydrous) | 36.6 |
| Cyclomethicone | 42.0 |
| Dimethicone | 8.0 |
| Cellulose ethyl ether | 2.0 |
| Dioxybenzone | 4.0 |
| Octyldimethylpara amino benzoate | 7.0 |
| Fragrance | 0.4 |
| | 100.0% |

The foregoing composition when spread on the skin, is quickly absorbed into the skin, leaving an elegant, greaseless, non-tacky, dry, film, providing a superior sun protection factor, and superior resistance to removal of the active agents from the skin by perspiration or water as evidenced by standard whirlpool wash-off tests.

While the present invention has been set forth in terms of specific embodiments thereof, it will be understood that numerous variations are now enabled to those skilled in the art. Accordingly, the invention is to be broadly construed and limited only by the scope of the appended claims.

What is claimed is:

1. A water-proof sunscreen composition consisting essentially of from 0.1% to 10.0% by weight of cellulose ethyl ether having an ethoxy content of about 43%, from 10.0% to 90.0% ethanol, propanol and isopropanol; from 1.0% to 20.0% by weight of an ultraviolet absorbing sunscreening agent and from 5.0% to 60.0% by weight of an emollient material selected from the group consisting of hydrocarbon oils, hydrocarbon waxes, fatty acid esters of low molecular weight alcohols and volatile silicone fluids.

2. A sunscreen composition as claimed in claim 1 wherein said solvent is ethanol.

3. A sunscreen composition as claimed in claim 1 wherein said ultraviolet absorbing sunscreening agent is a mixture of octyl-dimethylpara-amino-benzoate and dioxybenzone.

4. A sunscreen composition as claimed in claim 1 wherein said emollient is cyclomethicone.

5. A sunscren composition as claimed in claim 4 which additionally contains from 1.0% to 10.0% by weight of a plasticizer selected from the group consisting of polymethyl siloxanes, polyphenylsiloxanes and mixtures of polymethyl siloxanes with trimethyl siloxysilicate.

* * * * *